(12) United States Patent
Dewanjee

(10) Patent No.: US 7,419,654 B2
(45) Date of Patent: Sep. 2, 2008

(54) CHARGE NEUTRAL COMPLEXES OF PARAMAGNETIC METALS AS INTRACELLULAR MAGNETIC RESONANCE IMAGING CONTRAST AGENTS

(75) Inventor: Mrinal K. Dewanjee, 21904 Ivy Leaf Dr., Boyds, MD (US) 20841-4118

(73) Assignee: Mrinal K. Dewanjee, Boyds, MD (US)

( * ) Notice: Subject to any disclaimer, the term of this patent is extended or adjusted under 35 U.S.C. 154(b) by 42 days.

(21) Appl. No.: 11/242,064

(22) Filed: Oct. 4, 2005

(65) Prior Publication Data

US 2006/0078502 A1    Apr. 13, 2006

Related U.S. Application Data

(60) Provisional application No. 60/616,649, filed on Oct. 8, 2004.

(51) Int. Cl.
*A61B 5/055* (2006.01)
(52) U.S. Cl. .................. 424/9.361; 424/1.11; 424/1.65; 424/9.1; 424/9.3; 424/9.36
(58) Field of Classification Search .................. 424/9.3, 424/9.36, 9.361, 1.11, 1.65, 9.1
See application file for complete search history.

(56) References Cited

U.S. PATENT DOCUMENTS

| | | | | |
|---|---|---|---|---|
| 2,755,280 | A | * | 7/1956 | Feigin et al. ................. 514/187 |
| 4,443,426 | A | | 4/1984 | Thakur |
| 4,615,879 | A | * | 10/1986 | Runge et al. ................. 424/9.32 |
| 5,308,606 | A | * | 5/1994 | Wilson et al. .............. 424/1.65 |
| 5,312,617 | A | | 5/1994 | Unger et al. |
| 5,401,492 | A | * | 3/1995 | Kellar et al. ................. 424/9.32 |
| 5,466,438 | A | | 11/1995 | Unger et al. |
| 5,624,662 | A | | 4/1997 | Unger et al. |
| 5,762,910 | A | | 6/1998 | Unger et al. |
| 6,010,682 | A | | 1/2000 | Unger et al. |
| 6,146,614 | A | * | 11/2000 | Rubin et al. ................. 424/1.49 |
| 6,242,007 | B1 | | 6/2001 | Mohseni et al. |
| 6,685,913 | B1 | | 2/2004 | Thakur |

OTHER PUBLICATIONS

Ibrahim, S. et al., J. Inorg. Biochem., 1986, 28(1), p. 57-65.*
Giacometti, A. et al., Am. J. Neuroradiology, 1993, 14, p. 123-127 (abstract).*
Dewanjee et al., Investigative Radiology, vol. 19, No. 6, pp. 535-539 and 542, Nov.-Dec. 1984.
Dewanjee et al., Circulation, vol. 69, pp. 350-356 (1984).
Dietrich et al., "Platelet Accumulation After Carotid Thrombosis", Stroke, vol. 24, No. 10, pp. 1534-1540, Oct. 1993.
Holman et al., jnm/Concise Communication, vol. 14, No. 8, pp. 595-599, Jan. 9, 1973.
Dewanjee, "Assessment of Thrombosis in Vivo", Annals of the New York Academy of Sciences, vol. 516, pp. 541-571 (1987).

* cited by examiner

*Primary Examiner*—D. L. Jones

(57) ABSTRACT

A contrast agent for magnetic resonance imaging comprising a complex of a paramagnetic cation, preferably $Gd^{+3}$, $Dy^{+3}$, and $Fe^{+3}$ with three equivalents of a charge neutralizing chelator that provides a lipid soluble complex of the paramagnetic cation is described. The complex is retained intracellularly when introduced into a mammalian cell. A method of providing an image of an internal pathology of a patient by magnetic resonance imaging (MRI) by administering the MRI contrast agent or tagged cells to the patient and scanning the patient using magnetic resonance imaging to obtain visible images of the internal pathology of the patient is also set forth.

1 Claim, 1 Drawing Sheet

CHARGE NEUTRAL COMPLEXES OF PARAMAGNETIC METALS AS INTRACELLULAR MAGNETIC RESONANCE IMAGING CONTRAST AGENTS

CROSS-REFERENCE TO RELATED APPLICATIONS

This application claims priority to U.S. Provisional Application No. 60/616,649, filed Oct. 8, 2004, the entire contents of which are hereby incorporated by reference.

INVENTION MADE WITH U.S. GOVERNMENT FUNDING

The invention described in the present application was made with funding contributed by the Government of the United States. Thus, the Government of the United States may have certain rights in the invention.

FIELD OF THE INVENTION

This invention relates to compositions of matter which are useful as contrast agents for magnetic resonance imaging (MRI). The compositions of matter of this invention are charge neutral, lipid soluble complexes of paramagnetic cations with particular chelators. This invention also contemplates methods that make use of the novel contrast agents. Unlike conventional extra-cellular contrast agents, the contrast agents of the present invention penetrate into the cells, thus permitting higher spatial resolution in MRI processing.

BACKGROUND OF THE INVENTION

Medical technology makes use of many different types of imaging in order to assist in the visualization for diagnostic purposes of organs, cells, and other features internal to animal bodies. Among these different types of imaging technologies are: X-ray technology, including Computed Axial Tomography (CAT) scans; ultrasound technology; nuclear technologies, including: Single Photon Emission Computed Tomography (SPECT); Positron Emission Tomography (PET); scintigraphic imaging of cells labeled with radioactive materials; and magnetic resonance imaging (MRI). Each of these technologies is based upon significantly different scientific principles. The present invention relates to MRI, which makes use of magnetism and radiofrequency pulses to provide images of features internal to the bodies of mammals.

Conventional MRI contrast agents work on water outside the cells. Many human pathologies resulting from inherited or mutated genes and subsequent defective proteins are inside the cells. The interactions of these defective proteins having conformational changes with intracellular water in cytoplasm and organelles may be different in diseased cells. The MRI contrast agents of the present invention work on water inside the cells.

Current MRI technology makes use of a complex of gadolinium (Gd) with a single chain anion diethylenetriaminepentaacetate (DTPA) as a contrast agent. Schering AG, for instance, provides MAGNEVIST, an ionic formulation of Gd-DTPA. Amersham Health, Inc. provides OMNISCAN, a nonionic formulation of Gd-DTPA-bismethylamide. Upon intravenous administration, these contrast agents diffuse from the vascular space into extracellular or interstitial space of tissues.

Stem cells have been labeled with magnetic iron oxide nanoparticles (MION) and the paramagnetic iron oxide in the cells has then been tracked by MRI. See, e.g., Arbab, et al., "Efficient Magnetic Cell Labeling with Protamine Sulfate Complexed to Ferumoxides for Cellular MRI", Blood, 104: 1217-1223 (2004). After several cell divisions, the iron concentration in vivo is reduced by dilution with the endogenous iron pool, adversely affecting the signal/noise ratio. Iron also induces susceptibility artifacts in the MR images. Luminescent particles of zinc sulfide-coated cadmium selenide 1.5 to 8 nanometers in diameter, called "quantum dots", have been used in a similar manner, for tracking implanted stem cells by optical imaging. See, e.g., Dabbousi, et al., "(CdSe)ZnS Core-Shell Quantum Dots: Synthesis and Characterization of a Size Series of Highly Luminescent Nanocrystallites", J. Phys. Chem. B, 101:9463-9475 (1997). The Dabbousi et al. article is reflective of the state of the art with respect to the preparation and administration of quantum dots. Other transfection agents, e.g. green fluorescent proteins (GFP) are used in stem cell tracking by optical imaging. However, the foreign proteins in GFP-transfected cells are susceptible to immune attack in the body thus shortening their expected lifetimes. In addition, they could only be imaged in small animals, due to lower ability of tissue penetration of emitted light used for optical imaging.

DETAILED DESCRIPTION OF THE INVENTION

Figure 1:
FIG. 1 presents a T1-weighted MR image (coronal slice, thickness 1 mm) of a C3H mouse at 3 and 30 minutes after two intravenous administrations of Gd-(tris)pyrithione complex.

As outlined above, in spite of significant effort in academia and industry during the last three decades, there is a scarcity of sensitive and specific magnetic resonance imaging (MRI) contrast agents. The present invention provides a series of novel intracellular MRI contrast agents that provide access to tissue space and targeted imaging of human pathology not available from the conventional MRI contrast agent gadolinium diethylenetriamine pentaacetate (Gd-DTPA). Gd-DTPA (MAGNEVIST) was approved by the FDA in 1988 for human brain imaging studies.

MRI is routinely used for non-invasive in vivo evaluation of healthy and tumor-bearing subjects. The present invention enhances the signal to noise ratio in tumor tissues and in abscesses over surrounding normal tissues in order to meet the challenges of research and specific diagnosis. This invention enables the use of paramagnetic metal ions, e.g., dysprosium or gadolinium or iron, so that tagged leukocytes can be used for imaging the sites or primary tumors and metastases, sites of acute and chronic inflammation in abscesses, and sites of vascular plaques in patients. During MRI, the paramagnetic metals in the body enhance the relaxivity of radiofrequency-excited protons of water molecules. Combined use of the intracellular contrast agents of the present invention with conventional extra-cellular contrast agents such as Gd-DTPA enhances MRI sensitivity and specificity even more, thereby increasing the diagnostic potential of MRI.

MRI of vulnerable rupture-prone vascular plaques remains a significant challenge. Intra-arterial injection of charge neutral complex serves as a paving agent for imaging the vascular plaque. In addition, tagged neutrophils or monocytes provide specificity, since there is a higher turnover of these cells which ultimately results in their instability and rupture. See, e.g., Libby, P., The pathogenesis of atherosclerosis. Chapter 241, Section IV. Disorders of cardiovascular system. In "Harrison's Online Principles of Internal Medicine". McGraw Hill Companies, NY, 2003.

Tumors recruit new blood vessels to meet their metabolic demand for oxygen and other nutrients. The newly recruited tumor vasculature is leaky due to its loose endothelial junctions and loosely formed extracellular matrix proteins. This leakiness promotes higher delivery of MRI contrast agents to the tumor site. Contrast agent-induced MRI signal enhancement is achieved by the same mechanism used in the generation of clinical MRI angiograms. The contrast agent reduces signal saturation level due to shorter T1 relaxation time in comparison to healthy tissues.

Gd-DTPA, which is a negatively charged complex, has been used as an extracellular marker for image enhancement in diagnostic MRI studies in patients. However, extracellular space accounts for only 30% of tissue water, while 70% of the water in tissues is intracellular. This water is not accessible with current MRI contrast agents such as Gd-DTPA. Paramagnetic iron oxide particles have been used for phagocytic labeling of stem cells. Due to endogenous iron content and dilution after several cell cycles, however, stem cells labeled with iron oxide particles are difficult to trace when implanted in, e.g. primate brains. The MRI contrast agents of the present invention open a new window for non-invasive MRI imaging of tumors and abscesses and inflammation sites, by providing improved access to the previously unexplored intracellular water space.

Metal atoms become positively charged cations upon losing electrons from their outermost electronic orbitals. These cations cannot go through the lipid bilayers of cell membranes. However, by converting the metal cations of interest as MRI contrast agents into charge-neutral complexes, they can penetrate the cell membrane, thus providing a novel avenue of intracellular MRI signal enhancement in healthy circulating cells, cells of healthy organs and in cells of diseased tissues. For MRI studies, the present invention employs several milligrams of the paramagnetic metal ions, in the appropriate chemical form.

One embodiment of the present invention provides complexes of divalent or trivalent paramagnetic cations of a stable isotope ion with separate "small" chelators. The term "small" in this context is used to designate a chelator that is not spatially configured in the complex in a manner which would sterically hinder access of water molecules to the metal ion at the center of the complex. This access to the metal ion of water molecules permits the relaxivity which is necessary to enable magnetic resonance imaging. The chelators used in this invention are generally bidentate or tridentate. These chelators may be anionic after deprotonation, or they may simply have a strong dipole. Overall the complex is preferably charge neutral. Generally, all of the chelators complexing the trivalent cation will be identical, although mixtures of bidentate and/or tridentate chelators may be used herein.

A paramagnetic metal atom has one or more unpaired nucleons in the atomic nucleus, providing a half-integral "spin" quantum number. For metal complex MRI contrast agents, the MRI relaxation efficiency per molecule depends on the nature of the metal in the chelate complex and the size of the metal chelate complex. These contrast agents serve as relaxation sinks for the protons of adjacent water molecules. The metal complex lattice receives the energy from the protons excited by radiofrequency (RF) pulses. The present invention provides complexes in which the paramagnetic ions have significantly more free space than they have with Gd-DTPA complexes. This facilitates energy transfer, and provides increased imaging efficiency. The complexes of the present invention are soluble in lipids and provide relaxivities in the range 50-150 millimole$^{-1}$ second$^{-1}$. The gadolinium complexes of this invention, for instance, provide T1 relaxivity values of 80 per millimole per second and T2 values of 93 millimole$^{-1}$ second$^{-1}$. The complexes of the present invention are thus particularly useful as intra-cellular MRI contrast agents.

This invention provides complexes of divalent or trivalent paramagnetic cations with two or three equivalents, respectively, of charge neutralizing small chelators (e.g., bidentate or tridentate chelators). In accordance with the present invention, any paramagnetic ion of a stable isotope may be complexed with conventional small bidentate or tridentate chelators. Typical conventional paramagnetic ions are $Cr^{+3}$, $Co^{+2}$, $Mn^{+2}$, $Ni^{+2}$, $Fe^{+3}$, $Fe^{+2}$, $La^{+3}$, $Cu^{+2}$, $Gd^{+3}$, $Ce^{+3}$, $Tb^{+3}$, $Pr^{+3}$, $Dy^{+3}$, $Nd^{+3}$, $Ho^{+3}$, $Pm^{+3}$, $Er^{+3}$, $Sm^{+3}$, $Tm^{+3}$, $Eu^{+3}$, $Yb^{+3}$, and $Lu^{+3}$. Especially preferred paramagnetic cations in this invention are $Gd^{+3}$, $Dy^{+3}$, and $Fe^{+3}$. The complexes may be formed by reacting salts of the paramagnetic ions with the chelating agents. Among the metal salts that may be employed are chlorides, bromides, fluorides, iodides, and acetates, although those skilled in the art will readily appreciate that many other conventional metal salts could alternatively be employed.

The chelators that can be used in the present invention must bind the paramagnetic metal ion selected while providing a steric configuration to the complex which permits water molecules to move in and out of the complex. Typical small bidentate chelators that can be used in this invention include acetoacetone, oxine, tropolone, and pyrithione, although tridentate and other types of chelators may be used so long as they meet the steric and charge considerations discussed above. Preferably, the chelator is a bidentate chelator bearing a single negative charge, such as the chelators of oxine, tropolone, and pyrithione.

The reaction to form the complex is carried out simply by mixing the metal salt with the chelator. This reaction can be carried out in an aqueous medium and at room temperature. However, the temperature is not critical and, for example, temperatures from 4 to 90° C. may be utilized, if desired, in chelate formation. Some complexes may dissociate at higher temperatures. Hence, high temperatures should generally be avoided unless they are necessary for accelerating the chelation reaction.

The structure of a charge neutral divalent metal (tropolone)$_2$ complex is as follows:

Neutral Divalent Metal(tropolone)$_2$ Complexes

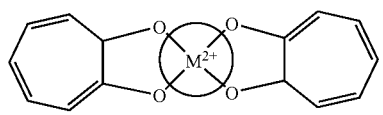

The structures of charge neutral trivalent metal(oxine)$_3$, metal(tropolone)$_3$ and metal (pyrithione)$_3$ complexes are shown below:

Charge Neutral Trivalent Metal(Oxine)$_3$ (8-hydroxy quinoline) Complexes $^{111}$In, $^{67,68}$Ga, Fe, Gd, Eu, Dy

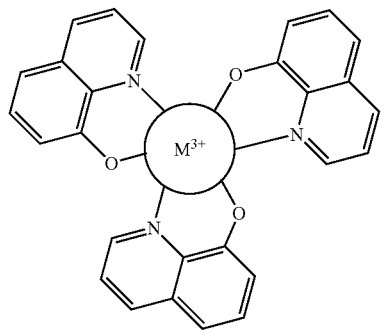

Charge Neutral Trivalent Metal(tropolone)$_3$ Complex

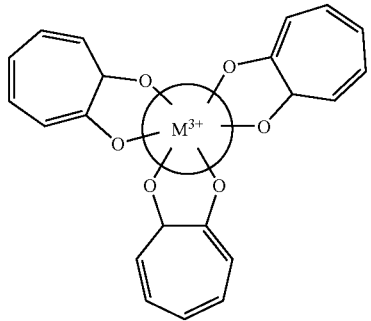

Charge Neutral Trivalent Metal-[pyrithione]$_3$/(2-mercaptopyridine 1-N-oxide)$_3$ Complexes

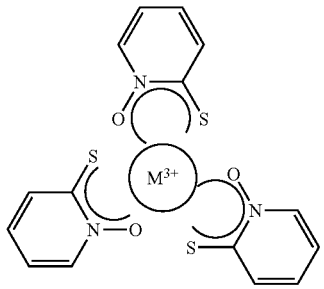

To prepare an in vivo diagnostic agent for imaging blood cells, the complex of this invention is reacted with the cells in vitro to label the cells for administration to the patient. The cells to be labeled can be, for instance, platelets, red blood cells, and white blood cells such as leukocytes, including neutrophils and lymphocytes or mixtures thereof. Separation of cells from whole blood is considered routine in, for example, the blood bank art. If one wishes to image, for instance, the leukocytes of a patient, one labels the leukocytes in vitro with the complex of this invention. Generally, it is preferred to label in vitro blood cells from the patient in whom the diagnostic imaging is to be carried out. However, one may label blood cells taken from a blood donor for performing imaging methods upon another person by matching blood types.

The types of cells to be labeled and imaged will depend on the condition to be diagnosed. For instance, if one wishes to diagnose vascular diseases such as thrombosis or to image platelet induced clotting in blood, one labels the platelets and injects the labeled platelets into the patient for detection of these vascular pathologies. If one wishes to diagnose internal infections and inflammations, one labels the white blood cells with a complex of this invention and injects these labeled white cells into the patient for imaging to diagnose internal infections and inflammations. Labeling lymphocytes with the complex of this invention provides an MRI contrast agent for imaging for detection of tumors and organ rejection.

Blood cells may be labeled with the complex of this invention by simply mixing the purified fraction of blood cells with the complex. Generally, this reaction will be carried out in the presence of plasma. However, any other conventional medium, such as saline, can also be used as the labeling medium. Non-chelating buffers such as phosphate-buffered saline, acetate-glucose, or isotonic saline itself generally provide close to 100% labeling efficiency. With plasma, the labeling efficiency decreases slightly, to 95-98%, with increasing concentration of plasma proteins. This decrease is lower with gadolinium complexes than it is with dysprosium complexes. The use of saline solution or organic solvents may alter or destroy the physiological functions of certain cell types; therefore these media may not always be appropriate. Labeling may typically be carried out by treating from about $0.5 \times 10^8$ cells to about $200 \times 10^8$ cells with the complex of this invention. This reaction can be carried out by simply mixing the cells to be labeled with the complex in a small volume of plasma or another medium that will maintain the viability of labeled cells.

The cells labeled by means of the paramagnetic metal complex of this invention can be injected intravenously into a patient for diagnostic imaging. In accordance with this invention, the complex-labeled cells are typically administered in a single unit injectable dose, which might be administered by an infusion technique as an alternative to rapid injection by syringe. Any of the carriers commonly utilized for such purposes, e.g., sterile isotonic saline solution, sterile heparinized, isotonic saline solution, acetate buffer, plasma, etc., can be employed for preparing the injectable solution. These media may also contain conventional pharmaceutical adjunct materials, such as pharmaceutically acceptable salts to adjust the osmotic pressure, buffers, preservatives, and the like. Generally, the unit dose to be administered contains about $50 \times 10^6$ to about $200 \times 10^8$ labeled blood cells. The solution to be injected in unit dosage form is typically from about 1 ml to about 10 ml in volume. After intravenous or intra-arterial administration, the labeled cells will image sites in vivo in a few minutes. However, imaging can be conducted, if desired, up to a few hours after injection. In most instances, an amount of the administered dose sufficient to permit MRI will accumulate in the area to be imaged within about 0.1 to 20, typically within 10 hours and more typically within 1 hour. In embodiments where stem cells are labeled and their survival and migration is observed, a time course of an experiment may be for several days or weeks after transplantation of the cells. Any conventional magnetic resonance imaging techniques may be utilized to carry out the present invention.

Without being bound by any theory of the invention, the lipid soluble complexes of the invention apparently pass through a cell membrane, and they bind to cytosolic protein(s) in the cell, trapping them within the cell.

Organ-imaging. The contrast agents of the present invention may be administered intravenously, intra-arterially, or intraperitoneally to obtain in vivo MRI scans of abscesses or tumors in animal organs.

Leukocyte labeling and imaging. The contrast agents of the present invention may be used to label leukocytes to diagnose infections and tumors in vivo.

Stem cell labeling and imaging. The contrast agents of the present invention may be used to label stem cells to evaluate the fate of transplanted stem cells in the brain, spinal column, heart, pancreas, or other organs. Stem cells may be labeled by the complexes directly, or the complexes may be coated onto quantum dots or other nanoparticles such as magnetic iron pyrithione particles, iron oxide particles, gadolinium oxide particles, or manganese oxide particles, and then the coated quantum dots or nanoparticles may be used to label the cells.

Vascular plaque imaging. The contrast agents of the present invention may be used to image vascular (coronary) plaque in animals, including humans.

Thrombus imaging. The contrast agents of the present invention may be used to image thrombi, by labeling platelets and injecting them intravenously or intra-arterially.

As indicated above, a method embodiment of this invention provides an image of an internal region of a patient by magnetic resonance imaging (MRI). This method involves administering to the patient a fairly large amount, e.g., up to 1.0 gram, of a paramagnetic ion in the form of an MRI contrast agent of the present invention. Subsequently, one scans the patient using magnetic resonance imaging in accordance with techniques that are familiar to those skilled in the art, in order to obtain visible images of the internal region of the patient. This method embodiment of the invention has many variants.

For example, it may provide an image using labeled leukocytes of a patient, for example at a site of inflammation, arterial plaque, tumors, or infection in the patient. This variant of the invention contemplates obtaining suitable leukocytes, for example by (i) removing whole blood from the patient and (ii) separating leukocytes from the blood, e.g., by centrifugation with Ficoll-Hypaque gradients or by filtration methods; then (iii) labeling the leukocytes with an MRI contrast agent of this invention, (iv) returning the labeled leukocytes to the patient's circulatory system, and (v) scanning the patient using MRI to obtain visible images of the labeled leukocytes accumulated at sites within the patient's body.

The method of the invention may provide images of thrombi in a patient using labeled platelets of the patient. In this method variant, one would obtain suitable platelets, for example by (i) removing whole blood from the patient and (ii) separating platelets from the blood; then (iii), label the platelets with the MRI contrast agent of the invention, (iv) return the labeled platelets to the patient's circulatory system, and (v) scan the patient using magnetic resonance imaging to obtain visible images of the labeled platelets accumulated at a site of thrombus formation within the patient's body.

Another aspect of the present invention is thus a method for imaging blood cells, e.g., red or white blood cells or platelets. In this method, an effective amount of a composition containing the blood cells to be imaged which have been labeled by means of a complex of a paramagnetic metal stable isotope with a charge neutralizing chelator that provides a lipid soluble complex of the paramagnetic cation, in a carrier suitable for intravenous or intra-arterial injection, are injected intravenously or intra-arterially, and then the area to be imaged is scanned with magnetic resonance imaging means.

As is well known to those skilled in the art, the amounts of MRI contrast agents to be administered for in vivo imaging are dependent upon the route of administration chosen and the need for regional concentration to permit imaging of a specific lesion or tissue compartment. Also, of course, one considers the toxicity of the particular MRI contrast agent involved. For intravenous use, and for intraperitoneal use, in a 70 kg patient, from 0.1-1 gram, preferably from 0.1 or 0.2 to 0.5 gram of the metal cation are typically employed in the form of a complex. For intra-arterial administration in a 70 kg patient, one usually uses from 0.05 to 0.5 grams of the cation selected (again in the form of a complex according to the invention). For cells tagged with paramagnetic ions in accordance with the present invention, much smaller amounts, in the range 0.01 to 0.2 milligram, are typically used. Thus, for example, for intravenous injection of metal-tagged neturophils, monocytes, lymphocytes, or stem cells in accordance with this invention, 0.05-0.1 milligrams of the metal ion are usually used. These small amounts are effective to enhance signal and signal/noise ratios during MRI because the cells localize, e.g., to infection lesions, vascular plaque sites, tumors, etc.

The present invention encompasses a method for providing an image of cancerous tissue in a patient, comprising (i) administering said contrast agent to a patient presenting with cancerous tissue, and (ii) scanning the patient using magnetic resonance imaging to obtain images of the cancerous tissue. The invention can also be used to image leukocytes or platelets within a patient by (i) labeling the leukocytes or platelets with said contrast agent in vitro, (ii) introducing the labeled leukocytes or platelets into the patient, and (iii) scanning the patient using magnetic resonance imaging to obtain visible images of the labeled leukocytes or platelets accumulated at sites within the patient.

In such a method, the leukocytes or platelets are commonly first separated from whole blood of the patient by centrifugation using a Ficoll-Hypaque gradient.

The labeled platelets can be used for imaging thrombi in a patient using labeled platelets of said patient comprising (i), labeling the platelets with said contrast agent in vitro, (ii) introducing the labeled platelets into the patient, and (iii) scanning the patient using magnetic resonance imaging to obtain visible images of the labeled platelets accumulated at the site of thrombus formation in the blood vessels of heart, brain or other vital organs or the chambers of heart of the affected patient.

The labeled leukocytes can be used for imaging arterial plaque, tumors, or infection in a patient, comprising (i) labeling leukocytes with said contrast agent in vitro, (ii) introducing the labeled leukocytes to the patient, and (iii) scanning the patient using magnetic resonance imaging to obtain visible images of the sites of accumulated labeled leukocytes in the patient.

In each of the above methods, it is preferred that the cells to be labeled are obtained from the patient into whom they are to be reintroduced.

The contrast agent of the invention can be used for tagging lipoproteins in the plasma of patients, in vitro, thus identifying the rupture-prone vulnerable coronary or carotid plaques by MRI.

In another embodiment, the invention encompasses a process for labeling blood cells comprising treating the blood cells to be labeled with a charge neutral, lipid soluble complex of a paramagnetic metal cation. Such a labeling method typicall includes a preliminary step of separating the blood cells to be labeled from serum. Preferably, the blood cells are treated with said complex in a glucose-acetate buffer solution.

In a very generic description, the present invention provides a method of conducting MRI which comprises the steps of:

providing a lipid soluble complex of a paramagnetic cation of the stable isotope with a charge neutralizing chelator, wherein said complex permits binding of the paramagnetic cation to cytosolic proteins and wherein said complex provides a relaxivity in the range 500-1500 per millimole per second;

treating cells of interest with said complex to obtain labeled cells;

introducing said labeled cell into a mammal; and imaging the mammal containing said cells with MRI.

In one embodiment, the living cells of interest are stem cells. The method of the invention may be used to capture images of labeled stem cells are accumulated over time to follow the survival and migration of the labeled cells after transplantation of stem cells into a mammalian body.

In such a method, the stem cells are contacted with the contrast agent to obtain complex-containing stem cells. Then the complex-containing stem cells are transplanted into the body of a mammal and magnetic resonance imaging is used to visualize locations of concentration of said stem cells in the mammal body over the course of time.

A preferred contrast agent for use in the above method is gadolinium (tris)pyrithione, dysprosium(tris)pyrithione, or ferric(tris)pyrithione.

The invention also provides a composition suitable for intravenous injection comprising a solution containing blood cells labeled with a complex of a paramagnetic metal cation stable isotope with a charge neutralizing chelator that provides a complex of said paramagnetic cation which is lipid soluble and which permits binding of the paramagnetic cation to cytosolic protein, said blood cells being suspended in a solvent suitable for intravenous injection. Such a composition may be formulated into a single injectable dose of from 1 ml to 10 ml and wherein said blood cells are present in the citrated-saline or citrated-plasma suspension in an amount of from $0.5 \times 10^8$ cells to $200 \times 10^8$ cells.

A preferred embodiment of such a composition is one in which the complex is gadolinium tris(pyrithione).

The contrast agent of the invention can be packaged into kit form. Conveniently, the complexes are formed as described herein, sterilized, filled into sterile bottles and then freeze-dried (lyophilized). The lyophilized complex is stable when stored for at least one year at 4° C. The lyophilized complex is reconstituted in acetate buffer (about 0.2 M NaOAc, pH 6.0 to 6.4) to the desired concentration for injection for use.

EXAMPLES

The MRI contrast agents of this invention may be evaluated using the human tumor implant model in nude mice. This tumor model is well accepted for studying tumor angiogenesis. Tagged human neutrophils are evaluated in the severe combined immune deficiency (SCID) mouse model. Quantitation and mapping of the paramagnetic ion at different times and by different routes permits determination of appropriate imaging times and routes for MRI procedures. All of these studies may be conducted on a 1.5, 3.0 or 7.0 Tesla 300 MHz MRI instrument (Bruker, Philips, GE, Siemens or Toshiba). Those skilled in the art, however, are well aware that similar studies may be conducted on instruments having other field strengths, e.g., on 1.0-7.0 Tesla instruments. Since movement distorts the quality of the MR image, before every imaging procedure, the mice are immobilized by injecting them with 0.2 ml of dilute ketamine-xylazine mixture. Xylazine (2.5 ml) is mixed with 10 ml of ketamine (conc.: 100 mg/ml). The mixture of ketamine and xylazine (2.5 ml) is diluted (1:4) with 10 ml of sterile saline. The mice are immobilized by anesthetizing them with 0.1-0.2 ml of the ketamine-xylazine mixture administered intraperitoneally with a 27-30 g needle. After imaging with the MRI instrument, and optionally with a gamma camera if imaging of a radioactive isotope label is desired, the mice may be anesthetized again with either 0.5 ml of ketamine-xylazine mixture or isoflurane inhalation and euthanized for dissection and further quantitative biodistribution study. Those skilled in the art are capable of varying any of the parameters selected as illustrative herein, in order to obtain similar or even optimized results.

Example 1

Synthesis of Gadolinium Pyrithione Complex

Ingredients. A stock solution of gadolinium trichloride, hexahydrate (Sigma-Aldrich, St. Louis, Mo.) at a concentration of 370 mg/ml in distilled and deionized water is prepared. The solution is sterilized by membrane filtration (0.22 micrometer filter, Millipore Inc., Bedford, Mass.) and the filtrate is stored in a refrigerator in a capped sterile polystyrene tube. A stock solution of pyrithione chelating agent at a concentration of 70 mg/ml in distilled and deionized water is prepared. The solution is sterilized by membrane filtration (0.22 micrometer filter) and the filtrate is stored in a refrigerator in a capped sterile polystyrene tube.

A stock solution of 0.2 molar acetate buffer is prepared by dissolving sodium acetate (Sigma-Aldrich) in distilled and deionized water. The pH is adjusted by adding acetic acid and sodium hydroxide to bring the solution to a pH of 6.8. The solution is sterilized by membrane filtration (0.22 micrometer filter) and the filtrate is stored in a refrigerator in a capped sterile polystyrene bottle. A solution of dextrose (Sigma-Aldrich) is prepared and mixed with the acetate buffer to a final concentration of 5 mg/ml to obtain acetate-dextrose buffer.

Complex Formation.

Fifty microliters of the gadolinium chloride solution is mixed with 250-400 microliters of the pyrithione solution. A white precipitate of gadolinium pyrithione complex is formed, which is vortexed for good mixing. The gadolinium pyrithione complex is dissolved in 1250 microliters of 0.2 molar acetate-dextrose buffer. The final pH is adjusted to 6.4 with a pH electrode (Beckman-Coulter). The osmolarity of the solution is checked by the freezing point method to 275 mOsmole. The gadolinium pyrithione complex solution is sterilized by membrane filtration (0.22 micrometer filter) and stored in a refrigerator.

This formulation is found to be stable after one year of storage in the refrigerator. It is soluble in 0.2 molar acetate buffer, in a mixture of acetate buffer and saline or human plasma facilitating the storage of Gd-complex, its transport and control of reconstitution by adjustment of injectate volume, and its use in cell-tagging and administration of tagged cells.

Example 2

Monitoring Complex Loading within a Body

During complexation, tracers of radioactive isotopes such as Gd-153 (2-10 microcuries) or Fe-59 (2-10 microcuries)

may be added as additional paramagnetic tracer cations. This enables quantitative tracing of the fate of the corresponding stable ion complexes. Harvesting and labeling efficiency of tagged cells such as leukocytes may be calculated from the radioactivity using a gamma-well counter (Wizard 1480, Perkin-Elmer, Inc.) and dose-calibrator (CRC-5, Capintec, Inc.). In a typical procedure, mice into which a tracer-labeled MRI contrast agent of this invention has been loaded may be immobilized by anesthetization with a ketamine-xylazine mixture (ketamine 100 mg and xylazine 150 mg in 5 ml of PBS, administered intraperitoneally with a 30 g needle). After imaging with a gamma camera, the mice may be anesthetized with either 0.1-0.2 ml of ketamine-xylazine mixture or isoflurane and euthanized by cervical dislocation. The mice may then be dissected and organs, tumors, abscesses, and tissues may be collected and weighed in a balance. The radioactivity due to the tracer ions in blood, urine, organs, and connective tissue may be measured for samples in a gamma-well-counter and the percent of injected dose/gram of organs and tissues may then be estimated. The effect of dosage, time-post injection, route of administration, and carrier level on biodistribution may then be analyzed.

Example 3

Kinetics of Gadolinium Complex Binding to Plasma Lipoproteins

For this study, the galadolinium pyrithione complex labeled with Gd-153 was incubated directly with isolated lipoprotein particles in acetate-citrate buffer or was incubated with intact plasma for 60 minutes at room temperature. Very low, low and high-density lipoproteins (VLDL, LDL and HDL) were separated by cesium chloride density gradients (1.06 and 1.25 g/ml) in an ultracentrifuge (Beckman L8-55) in a swinging bucket rotor using standard protocols. The mixture in 4.5 ml in polyallomer tubes was spun at 210,000 g for 20 hours. The plasma proteins in the top layer, and layers representing each of VLDL, LDL and HDL were removed from the top of the tube by suction. The amount of gadolinium pyrithione bound to VLDL, LDL, HDL and plasma proteins was measured by counting the radioactivity in each fraction with the gamma well counter. The majority of gadolinium complexes were bound to lipoproteins. Accordingly, the gadolinium-tagged lipoprotein particles are useful to localize the sites of vulnerable plaques in patients, thus identifying the rupture-prone vulnerable plaques in the coronary or carotid arteries with MRI.

Example 4

Kinetics of Complex Loading into Cells. For this study, human neutrophils were obtained from a single donor and suspended in 50 microliters of the same donor's plasma in a series of test tubes. The neutrophils were incubated at 37° C. with gadolinium pyrithione complex in a shaker bath. The amount of gadolinium pyrithione used for each test tube provided 3.7 mg of gadolinium, which was added to the test tube in 250 microliters of acetate buffer. After various incubation times, the neutrophil cells were centrifuged, washed with buffer and the amount of neutrophil-bound gadolinium was calculated. Gadolinium uptake as a function of time was as shown in Table 1:

TABLE 1

| Incubation Time (minutes) | Gadolinium (% in cells) |
|---|---|
| 05 | 99.21 |
| 10 | 99.75 |
| 30 | 99.36 |
| 45 | 99.11 |

This demonstrates both that gadolinium pyrithione complex provides rapid and efficient labeling (99.21% within 5 minutes) of human neutrophil cells, and that such labeling is persistent, that is, does not reverse itself as time passes (still 99.1 1% after 45 minutes).

Example 5

Relaxometry

The relaxivity provided by the complexes of this invention may be measured by the following procedure.

Sample Preparation.

A charge-neutralized complex in accordance with the present invention is prepared. Cells are tagged with the complexes and the molar concentration of the complexed metal in the tagged cells is determined. A typical embodiment incorporates 0.1-2.5 mg of paramagnetic metal ion in, e.g., 5-50 million white blood cells. After cell binding, these metals do not wash out, even after 48 hours or incubation time at room temperature or 37° C. Subsequent to incubation, serial dilutions of the tagged cells, suspended in 5% gelatin, are prepared. The serial dilutions are conducted to provide tagged cells at 10% and 1% of the original concentration. Each of the differently concentrated solutions of tagged cells is transferred into a borosilicate glass tube (Corning Inc., 10×75 mm).

Relaxometry.

For relaxometry studies, one may employ a variable field T1 and T2 analyzer. T1 refers to spin-lattice relaxation in the solid phase. T2 refers to spin-spin relaxation in the liquid phase. Preparatory to use, water flow for the cooling magnets and airflow for maintaining sample temperature are turned on. As a relaxivity standard, one may use glycerol or MAG-NEVIST. The sample is maintained at a temperature of 23° C. by the airflow. The frequency is tuned to 42.57 MHz. The magnetic field is set to 1.007 Tesla by means of the tuner, and then the tuner is turned off. The attenuation is set to 20 dB. Relaxivity in this embodiment measured at about 60 dB. T1 and T2 values are noted for each sample and relaxivity is determined by dividing the values obtained in this manner by the molar concentration of the samples in question.

Example 6

Imaging of Tumor Sites

Mouse flanks are prepared by cleaning with an alcohol swab. Ten million M21 cells in 100 μl of PBS are administered subcutaneously with a 27 g needle into both flanks of each mouse. M21 is a human melanoma cell line. The tumor growth in a nude mouse is monitored by measuring regional swelling with a pair of slide calipers. The gadolinium pyrithione complex is administered once the tumors have grown to 0.5-2.0 cm in any dimension.

The MRI contrast agent, tracer labeled with 2-10 microcuries of Gd-153, is prepared as in Example 1. Human neutrophils (25 million in 1.0 ml) are tagged with the MRI contrast agent and are administered intraperitoneally. The mouse is anesthetized with isoflurane, imaged with a 3.0 or 7.0 Tesla and 300 MHz MRI instrument, and is euthanized by cervical dislocation after exposure to carbon-dioxide gas in an enclosed chamber. Biodistribution of the gadolinium complex is analyzed by dissecting the mouse tissues and measuring the accumulation of Gd-153 radioactivity.

Example 7

Imaging of Inflammation Due to Bacterial Infection

Fresh human buffycoat preparations are obtained and leukocytes are separated out by Ficoll-Hypaque gradients (e.g. from Sigma, Inc., St. Louis, Mo.) in a laminar flow hood. Complete blood counts and differential white cell counts are performed with a cell counter (e.g. Abbott Cell Dyn 3500). The leukocytes (150-200 million) are labeled by incubation with gadolinium pyrithione complex for 60 minutes at 37° C. and centrifuged to remove any free gadolinium pyrithione complex. Tracer Gd-153 (2-10 microcuries) is added during complexation for tracing and quantitation of the fate of the corresponding stable complexes. The tagged leukocytes are resuspended in 1-2 ml of acetate-dextrose buffer. Harvesting and labeling efficiency and the Gd-level in tagged leukocytes are calculated from the radioactivity in a gamma-well counter (e.g. Wizard 1480, Perkin-Elmer, Inc.) and Dose-calibrator (e.g. CRC-5, Capintec, Inc.).

SCID mice are used in this study. Five million cells of *E. coli* (e.g. DH5-alpha, 100 µl in each flank) are administered subcutaneously into both flanks of each mouse. The growth of the abscess is monitored by measuring regional swelling with a pair of slide calipers. The gadolinium-containing leukocytes are administered intravenously once the abscesses have grown to 2 cm in any dimension. The mouse is anesthetized with isoflurane, imaged with a 3.0 or 7.0 Tesla and 300 MHz MRI instrument, and is euthanized by cervical dislocation. Biodistribution of the gadolinium complex is analyzed by dissecting the mouse tissues and measuring the accumulation of Gd-153 radioactivity.

Example 8

Biodistribution Upon Various Routes of Administration

The pharmacology of the novel MRI contrast agents is evaluated in healthy C3H mice upon administration by three different routes. Gadolinium pyrithione complex that is trace-labeled with 2-10 microcuries of Gd-153 is prepared as in Example 1. During intravenous and intra-arterial administration, the mouse is held inside a restrainer. For intraperitoneal administration, the mouse is held by the back of neck and the agent is injected into the peritoneum by lifting the skin of the abdomen. After administration, the mice are anesthetized with isoflurane, imaged with a 3.0 Tesla 300 MHz MRI instrument, and euthanized by cervical dislocation, some at 3, some at 24, and some at 72 hours post-administration. Biodistribution and biokinetics are evaluated by dissection of tissues and gamma-counting to determine the amount of accumulated gadolinium.

Example 9

Labeled Leukocytes

Fresh human buffycoat preparations are obtained. Leukocytes are separated by Ficoll-Hypaque gradients (Sigma, Inc., St. Louis, Mo.) in a laminar flow hood. The separated leukocytes are washed with 0.2 M acetate-buffered dextrose to remove the Ficoll-Hypaque reagent. Leukocytes (150-200 million) are incubated with gadolinium pyrithione for 60 minutes at 37° C. and centrifuged to wash away any free gadolinium pyrithione complex. The labeled leukocytes are resuspended in 1-2 ml of acetate-buffered dextrose.

Example 10

MRI Processing and Imaging of a Mouse

A Bruker 7.0 Tesla MRI System (BioSpin MRI Gmbh, Avance) operated at 300 MHz was used in this study. The system parameters are optimized for high resolution imaging with either T1-weighted (Gd-complexes) or T2-weighted agents (Fe-complexes). The mouse was placed on a stereotactic holder with a prone position. The holder stayed in the center of the 32 mm bore of the transmitter-receiver RF coil. The tail-vein was cannulated with a 27-29 G needle for delivery of contrast agents via slow infusion. 0.2 ml of 6 µM of the gadolium pyrithione complex was administered per dose. Two doses were administered 27 minutes apart. After acquisition of scout images, T1-weighted data were acquired with a spoiled gradient echo sequence, T1=100 to 700 ms, for example, 200 ms, TR (repetition time)=10 to 500 ms, for example, 13 ms, TE (echo time)=5 to 10 ms, for example, 6 ms, and flip angle=60-90 degree. Data were acquired before and after injection of contrast media to evaluate the reduction of tissue T1-values from 500-700 ms to 100-200 ms with the Gd-complexes or Gd-tagged cells.

FIG. 1 presents a T1-weighted MR image (coronal slice, 1 mm thickness) of the C3H mouse at 3 minutes after the second intravenous administration of Gd-(tris)pyrithione complex, providing an image at 3 and 30 minutes post administration. Note the localization Gd-(tris)pyrithione in the heart (Top) in the early phase post-IV injection (i.e. three minutes after the second administration) and bladder (bottom) in the late phase (i.e. thirty minutes after the first administration), demonstrating the in vivo stability of the agent. The conclusion that the complex is stable is reached because, unstable Gd-complexes hydrolyze and Gd-colloids form and localize in the macrophage pool of reticuloendothelial system of liver, spleen and bone marrow. None of these tissues were imaged in the present experiment.

T2-weighted data acquisition uses TR=1000-2500 ms and TE=15-25 ms for the T2-agents. A motion-suppression software is used to avoid the image distortion from the motion induced by breathing and respiration. Both static and dynamic images were acquired in a multi-slice e.g. 16-slice or 3D mode (128 slices for high resolution) for the evaluation of pharmacodynamics of contrast agents. Those skilled in the art will appreciate that other MRI systems are available, e.g., from GE Medical Systems, Toshiba, Siemens and Philips, and that the quantitative parameters used can be varied and optimized, depending upon factors including the organs, tissues, and specific pathologies, e.g., cancer, abscess, or inflammation, under investigation, and also depending upon whether the field strength is, e.g., 1.0 Tesla, 1.5 Tesla, 2.0 Tesla, 3.0 Tesla, 4.7 Tesla, 7.0 Tesla or some other higher value.

Various articles of the scientific periodical literature are cited herein. Each of these articles is hereby incorporated by reference in its entirety and for all purposes by such citation.

What is claimed is:

1. A method of magnetic resonance imaging (MRI) of a patient comprising:
   (i) administering to the patient about 0.01 to 0.2 mg of a paramagnetic ion in the form of a contrast agent comprising a gadolinium tris(pyrithione) complex in acetate buffer wherein said complex permits retention of the paramagnetic ions within diseased cells of a lesion in the patient, and
   (ii) scanning the patient using magnetic resonance imaging to obtain visible images of said lesion in affected organs and tissues.

* * * * *